US009228989B2

(12) United States Patent
Gerety et al.

(10) Patent No.: US 9,228,989 B2
(45) Date of Patent: Jan. 5, 2016

(54) SYSTEM AND METHOD FOR PERFORMING HEATER-LESS LEAD SELENIDE-BASED CAPNOMETRY AND/OR CAPNOGRAPHY

(75) Inventors: Eugene Peter Gerety, Seymour, CT (US); John Glaberson, Sandy Hook, CT (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 235 days.

(21) Appl. No.: 13/980,716

(22) PCT Filed: Jan. 20, 2012

(86) PCT No.: PCT/IB2012/050277
§ 371 (c)(1),
(2), (4) Date: Jul. 19, 2013

(87) PCT Pub. No.: WO2012/101556
PCT Pub. Date: Aug. 2, 2012

(65) Prior Publication Data
US 2013/0292570 A1   Nov. 7, 2013

Related U.S. Application Data

(60) Provisional application No. 61/435,912, filed on Jan. 25, 2011.

(51) Int. Cl.
*G01J 5/20* (2006.01)
*G01N 33/00* (2006.01)
*G01N 21/3504* (2014.01)
*A61B 5/08* (2006.01)

(52) U.S. Cl.
CPC ............ *G01N 33/0062* (2013.01); *A61B 5/082* (2013.01); *G01N 21/3504* (2013.01)

(58) Field of Classification Search
CPC .................... G01N 33/0062; G01N 21/3504
USPC .......................................... 250/338, 343–345
See application file for complete search history.

(56) References Cited

U.S. PATENT DOCUMENTS 4,907,166 A      3/1990  Corenman
5,281,817 A  *  1/1994  Yelderman et al. ........... 250/343
5,525,801 A  *  6/1996  Jacksen et al. ................ 250/352

FOREIGN PATENT DOCUMENTS

WO           9309413 A2      5/1993
WO      2004023997 A1      3/2004
WO      2007103855 A2      9/2007

OTHER PUBLICATIONS

Johnston, Sean F. "Gas Monitors Employing Infrared LEDs" Measurement Science and Technology, vol. 3, No. 2, 1992, pp. 191-195.

* cited by examiner

*Primary Examiner* — Constantine Hannaher
*Assistant Examiner* — Meenakshi Sahu

(57) ABSTRACT

A sensor device to detect a level of carbon dioxide in a body of gas includes one or more lead selenide detectors as infrared sensing elements. The sensor device operates without temperature regulation required by conventional lead selenide-based sensors, and instead measurements of the sensor device are compensated for a temperature measured by a thermal sensor.

17 Claims, 8 Drawing Sheets

SYSTEM AND METHOD FOR PERFORMING HEATER-LESS LEAD SELENIDE-BASED CAPNOMETRY AND/OR CAPNOGRAPHY

BACKGROUND

1. Field of the Disclosure

The disclosure relates to the performance of heater-less lead selenide based detection of carbon dioxide levels, and to calibration for temperature of a lead selenide detector.

2. Description of the Related Art

Sensor devices that implement Non-Dispersive Infrared (NDIR) gas analysis by means of lead selenide (PbSe) detectors that are sensitive to infrared radiation are known. Generally, these sensor devices employ heaters to maintain the temperature of the lead selenide detectors within very tight tolerances during operation. The regulation of temperature of the lead selenide detectors increases initialization time for users, increases the cost of manufacture and/or maintenance, and may adversely impact the longevity of these conventional devices.

Sensor devices that employ lead selenide detectors without heaters and temperature regulation generally use the detectors themselves to detect their own temperature. This is because a detector's "dark resistance" (i.e., the DC resistance of the detector in total darkness) is related to the detector's temperature, a phenomenon leveraged in such sensor devices.

SUMMARY

One aspect of the disclosure relates to a sensor device configured to measure a level of carbon dioxide in a body of gas. In one embodiment, the sensor device comprises a radiation source, a sensor, a processor, and a thermal sensor. The radiation source is configured to emit electromagnetic radiation through a body of gas. The sensor comprises a lead selenide detector arranged such that electromagnetic radiation emitted by the radiation source that has passed through the body of gas becomes incident on the lead selenide detector. The sensor is configured to generate a signal conveying information related to the intensity of electromagnetic radiation incident on the lead selenide detector. The processor is configured to determine a level of carbon dioxide in the body of gas based on the signal generated by the sensor. The thermal sensor is discrete from the lead selenide detector is configured to output a temperature signal conveying information related to a temperature of the lead selenide detector. The processor is further configured such that determination of the level of carbon dioxide involves a compensation for the temperature of the lead selenide detector as reflected in the temperature signal.

Another aspect of the disclosure relates to a method of detecting a level of carbon dioxide in a body of gas. In one embodiment, the method comprises emitting electromagnetic radiation through a body of gas; receiving electromagnetic radiation that has passed through the body of gas on a lead selenide detector; generating a sensor signal conveying information related to the intensity of electromagnetic radiation incident on the lead selenide detector; generating a temperature signal via a thermal sensor that is discrete from the lead selenide detector, the temperature signal conveying information related to the temperature of the lead selenide detector; determining a level of carbon dioxide in the body of gas based on the sensor signal, wherein determining the level of carbon dioxide in the body of gas involves a compensation for the temperature of the lead selenide detector as reflected in the temperature signal.

Yet another aspect of the disclosure relates to a system for detecting a level of carbon dioxide in a body of gas. In one embodiment, the system comprises means for emitting electromagnetic radiation through a body of gas; means for directing the electromagnetic radiation that has passed through the body of gas onto a lead selenide detector; means for generating a sensor signal conveying information related to the intensity of electromagnetic radiation incident on the lead selenide detector; means for generating a temperature signal that is discrete from the lead selenide detector, the temperature signal conveying information related to the temperature of the lead selenide detector; and means for determining a level of carbon dioxide in the body of gas based on the sensor signal, wherein determining the level of carbon dioxide in the body of gas involves a compensation for the temperature of the lead selenide detector as reflected in the temperature signal.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated herein are drawn to scale. It is to be expressly understood, however, that the drawings are for the purpose of illustration and description only and are not a limitation. In addition, it should be appreciated that structural features shown or described in any one embodiment herein can be used in other embodiments as well. It is to be expressly understood, however, that the drawings are for the purpose of illustration and description only and are not intended as a definition of limits. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
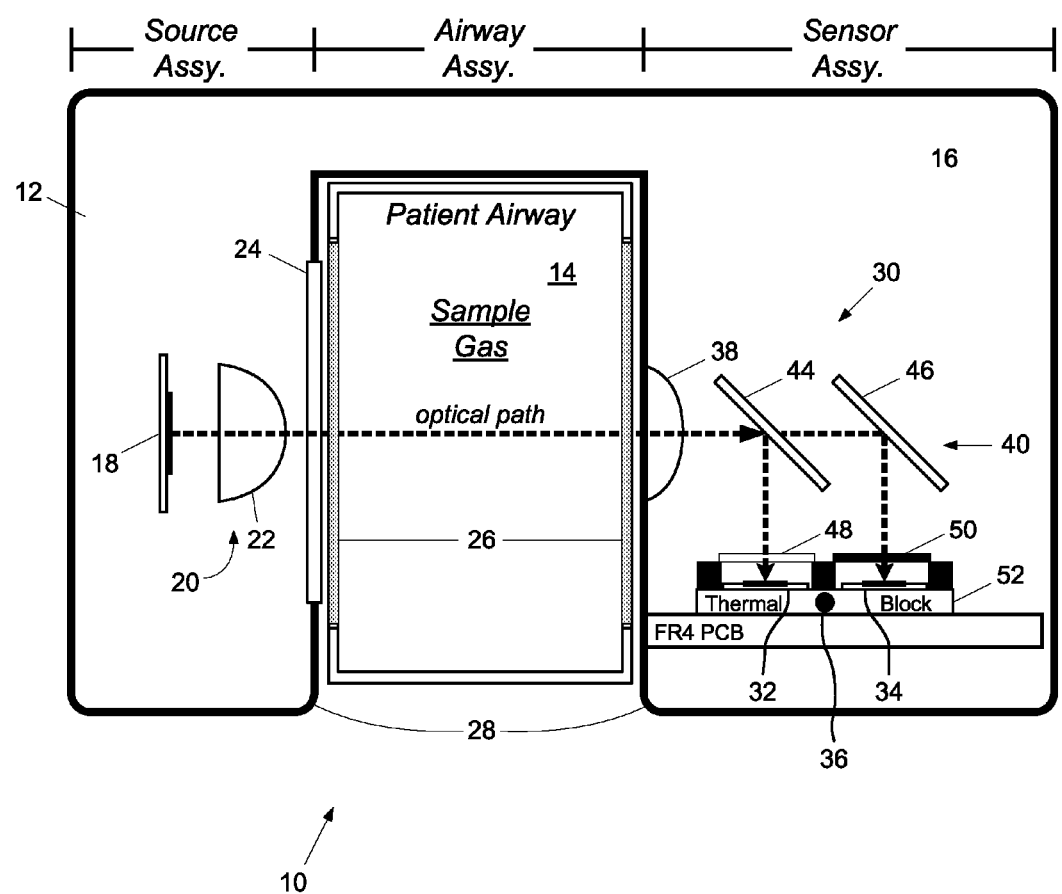
FIG. 1 illustrates a sensor configured to detect a level of carbon dioxide in a body of gas.

FIG. 1 illustrates a sensor device 10 configured to detect a level of carbon dioxide in a body of gas. The sensor device 10 employs lead selenide detectors (32 and 34), and operates without the temperature regulation required by conventional lead selenide-based sensor devices. Instead, measurements of sensor device 10 are compensated for variations in temperature. This may reduce the cost, enhance stability, enhance ruggedness, enhance manufacture and/or provide other advantages over conventional sensor devices. In one embodiment, sensor device 10 includes a "U" shaped housing 28 enclosing a source assembly 12, a hollow airway assembly 14, a detector assembly 16, and/or other components. Two opposing legs of the "U" shaped housing 28 define opposite sides of a gap therebetween, with the source assembly 12 disposed in one leg on one side of the gap (source side) and the detector assembly 16 disposed in the opposing leg on the opposite side of the gap (detector side). The sensor device 10 also includes self-contained electronics (not shown in FIG. 1) disposed within the housing 28.

The airway assembly 16 has windows 26 disposed on opposite sides such that infrared radiation entering the airway via the window 26 on one side of the airway 14 passes through a sample gas (patient respiration) in the airway 14 and exits via the window 26 on the opposite side. The airway assembly 14 may be either a disposable unit or a reusable unit that removably clips into the gap in the "U" shaped housing, with the source assembly 12 and detector assembly 16 being generally arranged such that infrared radiation emanating from the source assembly is directed across the gap through the gas sample in the airway assembly 14 to impinge upon the detector assembly 16. The airway windows 26 may be formed of plastic film (disposable version), sapphire (reusable version) and/or other materials.

The source assembly 12 includes a radiation source 18, optics 20, and/or other components. The emitter 18 may be driven by a pulsed source of energy to produce pulsed infrared radiation. The optics 20 may include a sapphire half-ball lens 22, a sapphire window 24, and/or other optical components. The radiation source 18 produces broadband radiation including an "MWIR" (Mid-Wavelength InfraRed) band. Infrared radiation generally refers to radiation occupying a band of wavelengths in the optical spectrum between 0.7 µm and 300 µm. "MWIR" generally refers to a mid-wavelength subset of the infrared radiation band between 3 µm and 8 µm. MWIR radiation emitted by the radiation source 18 includes a reference wavelength and a carbon dioxide wavelength ($\lambda_{REF}$ and $\lambda_{CO2}$, respectively). The radiation source 18 may be pulsed at about 100 Hz to produce a periodically varying MWIR signal with a period of about 10 milliseconds. The sapphire half-ball lens 22 gathers and collimates the emitted radiation, directing it across the gap and through the airway assembly 14 towards the detector assembly 16 via the sapphire window 24.

The detector assembly 16 includes optics 30, a first lead selenide detector 32, a second lead selenide detector 34, a thermal sensor 36, and/or other components. The optics 30 comprise a lens assembly 38, a beam splitter assembly 40, and/or other optical components. The lens assembly 38, which in one embodiment includes an AR-coated (Anti-Reflective coated) silicon plano-convex lens, focuses the MWIR radiation reaching it from the source assembly 12, and directs the electromagnetic radiation toward first lead selenide detector 32 and second lead selenide detector 34 via beam splitter assembly 40. In beam splitter assembly 40, a dichroic beamsplitter 44 is positioned to reflect IR radiation containing the carbon dioxide wavelength $\lambda_{CO2}$ towards first lead selenide detector 32, and to pass IR radiation containing the reference wavelength $\lambda_{REF}$ towards second lead selenide detector 34 via a turning mirror 46. A narrow-band first optical filter 48 that passes $\lambda_{CO2}$ is positioned in front of first lead selenide detector 32. A narrow-band second optical filter 50 that passes $\lambda_{REF}$ is positioned in front of second lead selenide detector 34.

In detector assembly 16, first lead selenide detector 32 and second lead selenide detector 34 are mounted to a thermal block 52. The thermal sensor 36 is thermally coupled (e.g., mounted) to first lead selenide detector 32, second lead selenide detector 34, and/or thermal block 52. The thermal sensor 36 may have more relaxed specifications and/or reduced accuracy than thermal sensors implemented in conventional lead selenide-based detectors that regulate the temperature of the lead selenide members. This is because in compensating detector responses for temperature-related effects, it is only necessary that the thermal sensor provide highly repeatable measurements; absolute accuracy is not required. Typically, highly "accurate" thermal sensors are selected, trimmed or otherwise characterized to provide close conformance to a specific temperature vs. resistance curve. Despite their absolute accuracy, however, the repeatability of measurements made by such "accurate" thermal sensors is not significantly different from the repeatability of similar, but less "accurate" thermal sensors. It will be appreciated that although thermal sensor 36 is illustrated in FIG. 1 as a single thermal sensor, this is not intended to be limiting and this disclosure covers embodiments in which a plurality of thermal sensors are implemented to monitor temperature of components in detector assembly 16. For example, in one embodiment, thermal sensor 36 includes a pair of thermal sensor units that separately monitor the temperatures of first lead selenide detector 32 and second lead selenide detector 34 individually.

The basic principle of operation behind Capnometry/Capnography via sensor device 10 is that infrared radiation in a band around 4.275 µm experiences increasing absorption (when traveling a fixed-length path through a sample gas) with increasing carbon dioxide concentration—according to a reliably repeatable relationship. By way of comparison, the absorption of 3.681 µm infrared radiation under the same conditions is essentially unaffected by carbon dioxide concentration.

When the MWIR radiation from radiation source 18 passes through the body of gas in airway assembly 14, IR radiation at $\lambda_{CO2}$ is attenuated according to the concentration of carbon dioxide in the body of gas. IR radiation at $\lambda_{REF}$, however, is unaffected by any carbon dioxide in the body of gas, and varies only with the intensity of the IR radiation from radiation source 18. Since $\lambda_{REF}$ and $\lambda_{CO2}$ are fairly close together on the black-body radiation curve, the output signals of first lead selenide member 32 and second lead selenide member 34, which are sensitive to IR electromagnetic radiation, will be approximately proportional to one another over small variations in source radiation intensity as long as carbon dioxide concentration in the body of gas remains constant. By "zeroing" sensor device 10 with $N_2$ (or with room air—after making appropriate compensation for residual carbon dioxide in the atmosphere), a reference ratio between the output signal levels from first lead selenide detector 32 and second lead selenide detector 34 is established. Whenever the ratio between the two signals is equal to this reference ratio, there is no carbon dioxide in airway assembly 14. Any decrease in the output signal of the first lead selenide detector 32 relative to output signal of second lead selenide detector 34 indicates a corresponding increase in the concentration of carbon dioxide in airway assembly 14.

Figure 2:
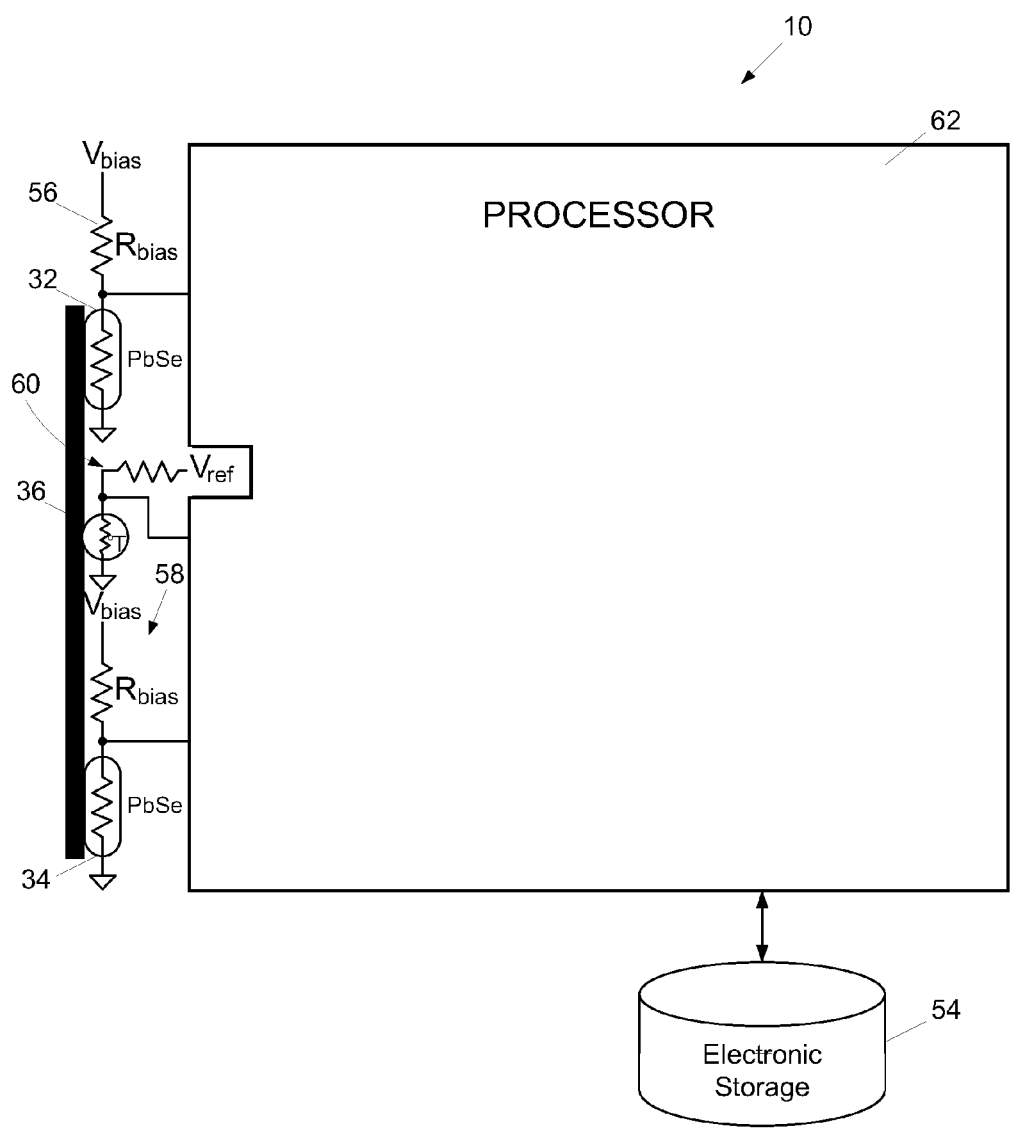
FIG. 2 illustrates sensing elements of a sensor configured to detect a level of carbon dioxide in a body of gas.

FIG. 2 illustrates at least some of the electronic components associated with sensor device 10. These components include electronic storage 54, first lead selenide detector 32, second lead selenide detector 34, thermal sensor 36, a first sensor circuit 56, a second sensor circuit 58, a thermal sensor circuit 60, a processor 62, and/or other components.

Electronic storage 54 comprises electronic storage media that electronically stores information. The electronic storage media of electronic storage 54 may include one or both of system storage that is provided integrally (i.e., substantially non-removable) with sensor device 10 and/or removable storage that is removably connectable to sensor device 10 via, for example, a port (e.g., a USB port, a firewire port, etc.) or a drive (e.g., a disk drive, etc.). Electronic storage 54 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 54 may include virtual storage resources, such as storage resources provided via a cloud and/or a virtual private network. Electronic storage 54 may store software algorithms, information determined by processor 62, and/or other information that enables sensor device 10 to function properly. Electronic storage 54 may be a separate component within system 10, or electronic storage 54 may be provided integrally with one or more other components of sensor device 10 (e.g., processor 62).

The first lead selenide detector 32 and first sensor circuit 56 form a first detection unit configured to generate a first sensor signal. The first sensor signal conveys information related to the intensity of electromagnetic radiation that is incident on first lead selenide detector 32. The bias voltage ($v_{bias}$) applied to the first sensor circuit 56 is a DC voltage. It will be appreciated that one or more of the circuit components illustrated in FIG. 2 as being included in first sensor circuit 56 may be provided virtually (e.g., by processor 62).

The second lead selenide detector 34 and second sensor circuit 58 form a second detection unit configured to generate a second sensor signal. The second sensor signal conveys information related to the intensity of electromagnetic radiation that is incident on second lead selenide detector 34. The bias voltage ($v_{bias}$) applied to second sensor circuit 58 is a DC voltage, which may be the same as the bias voltage applied to first sensor circuit 56. It will be appreciated that one or more of the circuit components illustrated in FIG. 2 as being included in first sensor circuit 56 may be provided virtually (e.g., by processor 62).

Note that the detector bias configuration shown in FIG. 2 is not intended to be limiting. Rather, it is illustrative of any of several possible bias configurations. For example, in the bias configuration shown, the voltage across the detector varies as the detector resistance varies (with temperature). An alternative bias configuration would connect one end of the detector to a negative bias voltage, and the other end of the detector to a summing junction of an operational amplifier configured as an inverting amplifer. In this way, an output signal representative of the detectors resistance (sum of AC and DC responses) would be produced at the output of the operational amplifier, with the bias voltage across the detector remaining constant even with changing detector resistance The thermal sensor 36 and thermal sensor circuit 60 form a temperature sensor configured to generate a temperature signal conveying information related to the temperature of first lead selenide detector 32 and/or second lead selenide detector 34. In an embodiment in which sensor device 10 includes two separate thermal sensors, each monitoring an individual one of first lead selenide detector 32 and second lead selenide detector 34 separately from the other, the sensor device 10 may further include a second thermal sensor circuit which operates with the second thermal sensor to generate a second temperature signal.

Processor 62 is configured to provide information processing capabilities in sensor device 10. As such, processor 62 may include one or more of a digital processor, an analog processor, a digital circuit designed to process information, an analog circuit designed to process information, a state machine, and/or other mechanisms for electronically processing information. Although processor 62 is shown in FIG. 2 as a single entity, this is for illustrative purposes only. In some implementations, processor 62 may include a plurality of processing units. These processing units may be physically located within the same device, or processor 62 may represent processing functionality of a plurality of devices operating in coordination. Processor 62 may be configured to execute one or more modules. Processor 62 may be configured to execute the modules by software; hardware; firmware; some combination of software, hardware, and/or firmware; and/or other mechanisms for configuring processing capabilities on processor 62.

The processor 62 is configured to determine the level of carbon dioxide in the body of gas within airway assembly 14. The processor 62 determines the level of carbon dioxide in the body of gas based on the first and second sensor signals. The determination of the level of carbon dioxide is compensated for the temperature of first lead selenide detector 32 and/or the temperature of second lead selenide detector 34. As such, the temperature of first lead selenide detector 32 and/or the temperature of second lead selenide detector 34 may be allowed to drift with air temperature within sensor device 10. The sensor device 10 may be free of any heating or cooling elements for actively controlling the temperature of first lead selenide detector 32 and/or second lead selenide detector 34. This may reduce the cost of sensor device 10, enhance the precision and/or ruggedness of sensor device 10, reduce or eliminate an initialization time required by sensor device 10 upon activation, and/or provided other enhancements over conventional devices.

The level of carbon dioxide in the body of gas is directly proportional to a ratio of the first sensor signal to the second sensor signal. The processor 62 is to adjust this ratio to compensate for changes caused by changes in the temperature of first lead selenide detector 32 and/or second lead selenide detector 34. For example, processor 62 may implement the following relationship to adjust the ratio:

$$\text{RATIO} = k_{RATIO}\left[\frac{v_{CO2}(\max) - v_{CO2}(\min)}{v_{REF}(\max) - v_{REF}(\min)}\right] \cdot CF(T); \quad (1)$$

where kRATIO represents a scale factor constant (which can be embedded into CF(T)), vCO2 represents the voltage of the first sensor signal, vREF represents the voltage of the second sensor signal, and CF(T) represents a correction factor that varies as a function of temperature (or of the temperature signal(s)). The processor 62 is configured to determine the correction factor based on the temperature signal(s) output via thermal sensor 36. It will be appreciated that the compensation for temperature may be accomplished in some form other than compensation of the ratio. For example, one or both of the detector signals could be compensated individually. The description of the compensation of the ratio described herein is not intended to be limiting.

In order to compensate measurements taken by sensor device 10, the individual sensors formed using first lead selenide detector 32 and second lead selenide detector 34 must be calibrated for temperature. In one embodiment, to accomplish this, the lead selenide detectors 32 and 34 and thermal sensor(s) 36 are assembled into a tightly coupled (thermally) unit so that temperature readings taken from the thermal sensor(s) 36 are repeatable and relatively closely correlated with the actual temperature of the detectors 34 and 36. Note that a similar arrangement can be configured with separate thermal sensors for each detector. In this case, two detector/thermal sensor assemblies would be configured as separate thermal units, with each thermal sensor tightly coupled (thermally) to its respective detector.

Figure 3:
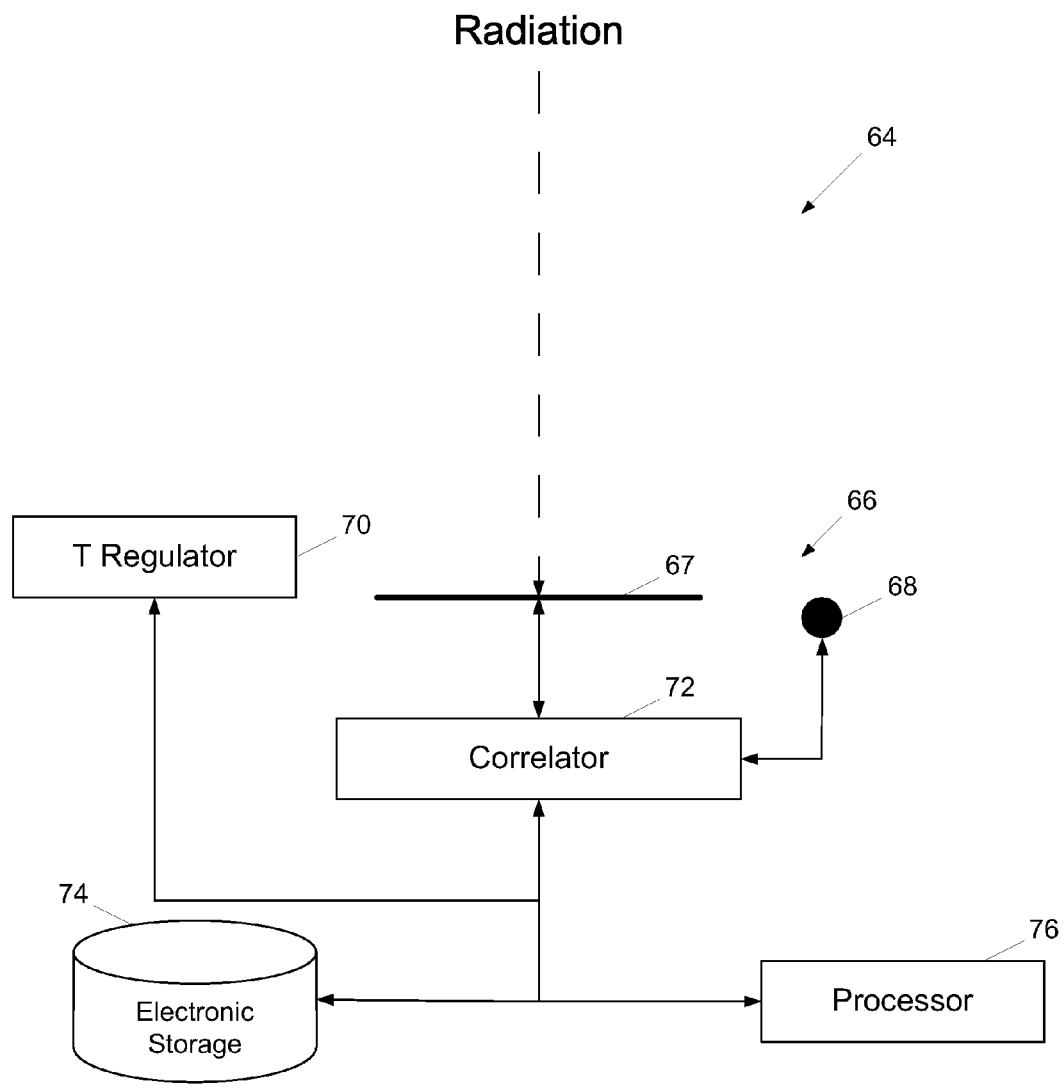
FIG. 3 illustrates a system configured to calibrate a lead selenide detector in a sensor configured to detect a level of carbon dioxide in a body of gas.

FIG. 3 illustrates a system 64 configured to calibrate a detector subassembly 66 for temperature by means of a thermal sensor 68. The detector subassembly 66 includes a lead selenide detector 67 and the thermal sensor 68 arranged into a tightly coupled thermal unit, as described hereinabove. The system 64 is configured to enhance calibration of detector subassembly 66 by calibrating detector subassembly 66 based on the output signals of the detector 67 and thermal sensor 68 as the detector subassembly moves from a first temperature to a second temperature as a unit. In one embodiment, the temperature of detector 67 is controlled (e.g., to the first temperature and/or the second temperature) without a localized point heating or cooling source, such that any difference in temperature (gradient) between the detector 67 and thermal sensor 68 is small and relatively immune to outside influence. The system 64 comprises a thermal sensor 68, a temperature regulator 70, a correlator 72, electronic storage 74, a processor 76, and/or other components.

It will be appreciated that in one embodiment lead selenide detector 67 shown in FIG. 3 actually represents two separate lead selenide detectors (e.g., similar to or the same as first lead selenide detector 32 and/or second lead selenide detector 34 shown in FIGS. 1 and 2). The two separate lead selenide detectors may be calibrated together, or separately.

The thermal sensor 68 is configured to generate a temperature signal conveying information related to the temperature of lead selenide detector 67. The thermal sensor 68 may be provided integrally with sensor 66, may be part of a fixture used to hold sensor 66 and/or lead selenide detector 67 during calibration, and/or may otherwise be provided. In one embodiment, thermal sensor 68 is similar to or the same as thermal sensor 36 shown in FIGS. 1 and 2 and is carried by sensor 66. In this embodiment, thermal sensor 68 may be used by sensor 66 during deployment to monitor the temperature of lead selenide detector 67. In one embodiment in which lead selenide detector 67 represents two separate lead selenide detectors, thermal sensor 68 includes a separate sensor for each of the lead selenide detectors.

The temperature regulator 70 is configured to regulate the temperature of lead selenide detector 67. The temperature regulator 70 may include a heater, a cooler, and/or other temperature regulators. The temperature regulator 70 may exchange heat with lead selenide detector 67 via conduction, convection, and/or via other heat exchange phenomena. In one embodiment, temperature regulator 70 includes one or more resistors in contact with lead selenide detector 67 that heat lead selenide detector 67 through conduction. In one embodiment, temperature regulator 70 includes a mechanism for heating or cooling the air around lead selenide detector 67.

During operation, temperature regulator 70 is configured to control the temperature of lead selenide detector 67 such that the temperature varies over a range of temperatures over time. The range of temperatures may be bounded by a first temperature and a second temperature. Controlling the temperature of detector 67 may include heating and/or cooling detector 67 such that the temperature of detector 67 sweeps over the temperatures between the first temperature and/or the second temperature.

The correlator 72 is configured to correlate samples of the sensor signal generated by sensor 66 with contemporaneous samples of the temperature signal generated by thermal sensor 68. The correlated samples provide the basis for determining a compensation to the sensor signal as a function of the temperature of lead selenide detector 67. In one embodiment, correlator 72 includes a lock-in amplifier that synchronizes collection of samples of the sensor signal and the temperature signal. The synchronization of the sample collection may be further synchronized to other events. For example, the correlator 72 may be configured to correlate samples of the sensor signal and the temperature signal with pulses of electromagnetic radiation that become incident on lead selenide detector 67. This may include synchronizing collection of the samples to a chopper (not shown) that chops the electromagnetic radiation emitted by a source (not shown).

Electronic storage 74 comprises electronic storage media that electronically stores information. The electronic storage media of electronic storage 74 may include one or both of system storage that is provided integrally (i.e., substantially non-removable) with system 64 and/or removable storage that is removably connectable to system 64 via, for example, a port (e.g., a USB port, a firewire port, etc.) or a drive (e.g., a disk drive, etc.). Electronic storage 74 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 74 may include virtual storage resources, such as storage resources provided via a cloud and/or a virtual private network. Electronic storage 74 may store software algorithms, information determined by processor 76, and/or other information that enables system 64 to function properly. Electronic storage 74 may be a separate component within system 64, or electronic storage 74 may be provided integrally with one or more other components of system 64 (e.g., processor 76).

Processor 76 is configured to provide information processing capabilities in system 64. As such, processor 76 may include one or more of a digital processor, an analog processor, a digital circuit designed to process information, an analog circuit designed to process information, a state machine, and/or other mechanisms for electronically processing information. Although processor 76 is shown in FIG. 3 as a single entity, this is for illustrative purposes only. In some implementations, processor 76 may include a plurality of processing units. These processing units may be physically located within the same device, or processor 76 may represent processing functionality of a plurality of devices. Processor 76 may be configured to execute one or more modules. Processor 76 may be configured to execute the modules by software; hardware; firmware; some combination of software, hardware, and/or firmware; and/or other mechanisms for configuring processing capabilities on processor 76.

The processor 76 is configured to determine a compensation that compensates for changes in the sensor signal caused by changes in temperature of lead selenide detector 67. The processor 76 is configured to determine the compensation based on the correlated samples of the sensor signal and the temperature signal. As the temperature of lead selenide detector 67 varies between the first temperature and the second temperature, the correlated sensor and temperature signals provide data used by processor 76 to determine the compensation.

Figure 4:
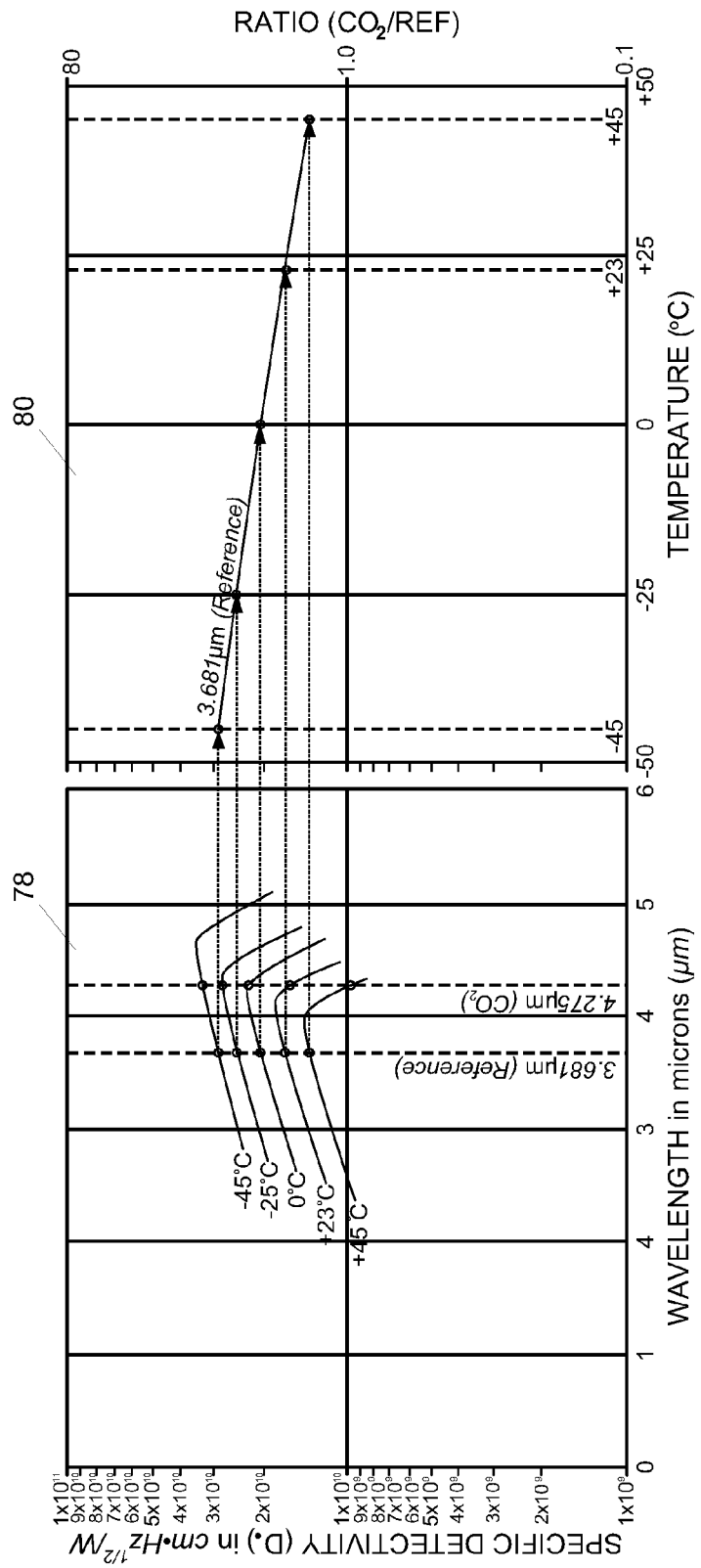
FIG. 4 illustrates plots of sensitivity of a typical lead selenide detector with respect to temperature, at a first (reference) wavelength.

By way of illustration, FIG. 4 illustrates a plot 78 of the spectral response of a lead selenide detector at a plurality of different temperatures, juxtaposed with a plot 80 of detector response (vertical axis) vs. temperature (horizontal axis). The plots 78 and 80 are arranged so that the vertical scale of the plots 78 and 80 is the same. This is done to facilitate graphical representation of the transfer of points from plot 78 to the plot 80. The marked intersection points for the reference wavelength $\lambda_{REF}$ from plot 78 are then transferred graphically to plot 80. The resulting plot 80 shows that detector responsivity at the reference wavelength $\lambda_{REF}$ decreases with increasing temperature.

Figure 5:
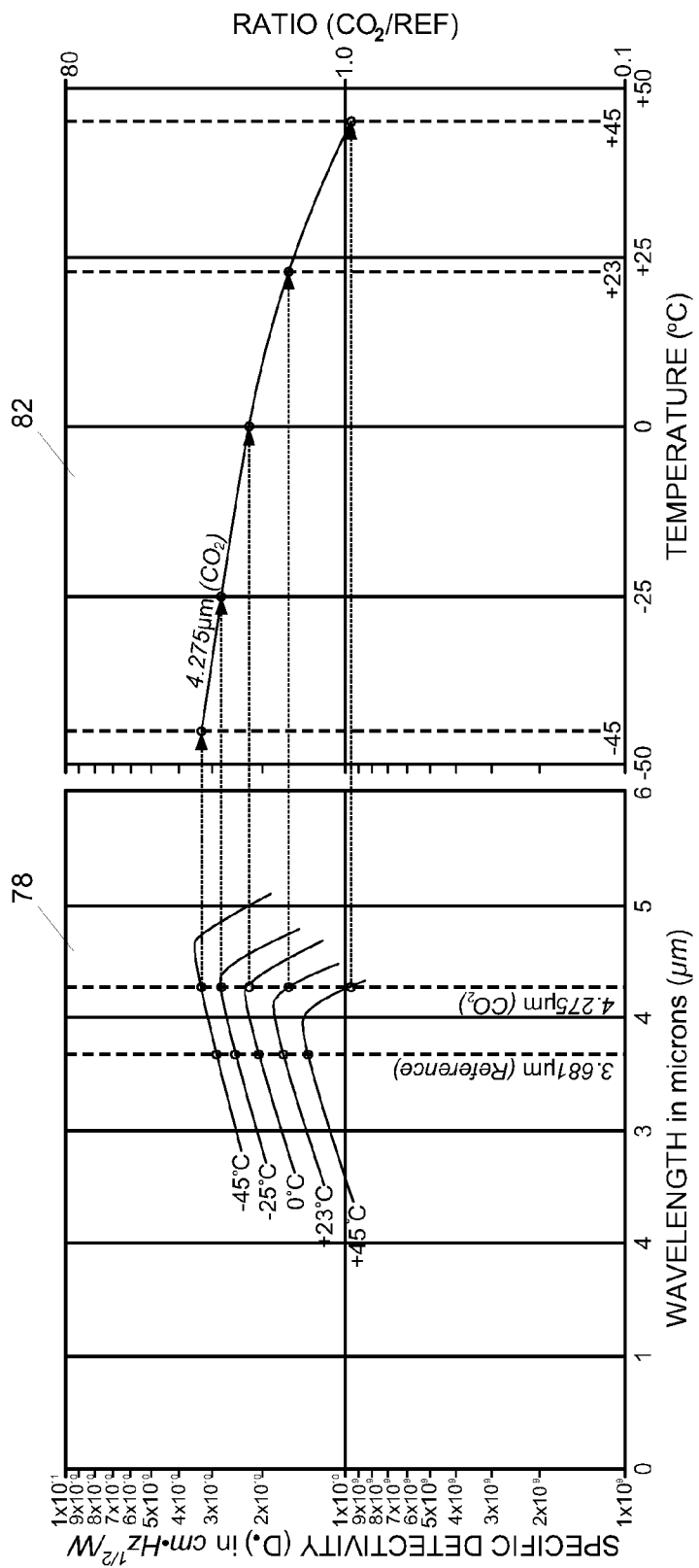
FIG. 5 illustrates plots of sensitivity of a typical lead selenide detector with respect to temperature, at a second (carbon dioxide sensing) wavelength.

In similar fashion, FIG. 5 repeats plot 78 juxtaposed with a plot 82 of detector response vs. temperature at wavelength $\lambda_{CO2}$. As before, the vertical scale of plots 78 and 82 is made the same to facilitate transfer of points from plot 78 to the plot 82. As with 80 shown in FIG. 4, plot 82 of FIG. 5 shows a detector response at $\lambda_{CO2}$ that also decreases with increasing temperature, but with a steeper downward slope than the $\lambda_{REF}$ response.

Figure 6:
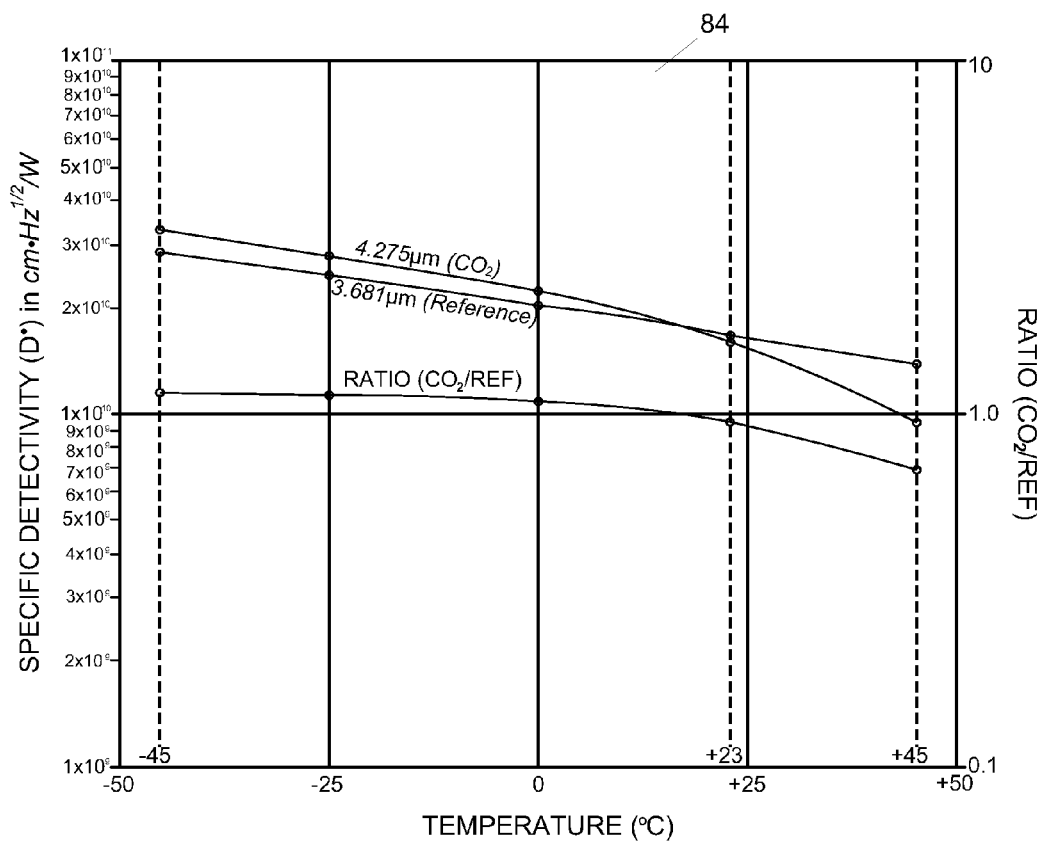
FIG. 6 illustrates a plot that compares sensitivity of a typical lead selenide detector with respect to temperature at the first and second wavelengths.

FIG. 6 is a composite plot 84 showing a first response curve 86 from FIG. 4 and a second response curve 88 from FIG. 5 overlaid on plot 84. In FIG. 6, the numeric ratio between the two curves calculated and plotted as curve 90 against the two response curves 86 and 88. Like the individual detector responsivity curves 86 and 88 at $\lambda_{CO2}$ and $\lambda_{REF}$, respectively, the ratio curve 90 shows a significant temperature dependency.

Returning to FIG. 3, in determining the compensation, processor 76 may be configured to determine a reference ratio $k_{ref}$. The reference ratio $k_{ref}$ may be determined in accordance with the following relationship:

$$k_{ref} = \frac{v_{REFm0}}{v_{CO2m0}}; \qquad (2)$$

where $v_{CO2m0}$ represents a sample of a first sensor including a first lead selenide detector represented by lead selenide detector 67 (e.g., receiving electromagnetic radiation at $\lambda_{CO2}$); and $v_{REFm0}$ represents a sample of a second sensor including a second lead selenide detector represented by lead selenide detector 67 (e.g., receiving electromagnetic radiation at $\lambda_{REF}$). The relationship for determining $k_{ref}$ set forth above may be implemented in an embodiment in which thermal sensor 68 includes a separate sensing device for each of the lead selenide detectors represented by lead selenide detector 67. If thermal sensor 68 includes only a single sensing device, $k_{ref}$ may be determined accordance with the following relationship:

$$k_{ref} = \frac{v_{CO2m0}}{v_{REFm0}}. \qquad (3)$$

In one embodiment, in which thermal sensor 68 includes a separate sensing device for each of the lead selenide detectors, processor 76 is configured to define, from the correlated signal samples, the following "best fit" continuous functions:

$$v_{CO2}(T_{CO2}); \text{ and} \qquad (4)$$

$$v_{REF}(T_{REF}); \qquad (5)$$

where $v_{CO2}$ ($T_{CO2}$) represents a first sensor signal from the sensor including the first lead selenide detector as a function of a first temperature signal output by a first temperature sensing device represented by thermal sensor 68, and $v_{REF}$ ($T_{REF}$) represents second sensor from the sensor including the second lead selenide detector as a function of a second temperature signal output by a second temperature sensing device represented by thermal sensor 68.

From these functions, processor 76 defines the compensation as a function of the first temperature signal and the second temperature signal as follows:

$$CF(T_{CO2}, T_{REF}) = \frac{v_{REF}(T_{REF})}{k_{ref} v_{CO2}(T_{CO2})}. \qquad (6)$$

In one embodiment, in which thermal sensor 68 includes a single sensing device for both of the lead selenide detectors, processor 76 is configured to define a new set of sample values ($v_{RATIOm}$):

$$v_{RATIOm} = \frac{v_{REFm}}{v_{CO2m}}; \qquad (7)$$

where $v_{REFm}$ represents the value of $v_{REF}$ at a sample m, and $v_{CO2m}$ represents the value of $v_{CO2}$ at sample m. The processor 76 is configured to then define the compensation as a best fit of the functional relationship between $V_{RATIOm}$ and $T_m$ as follows:

$$CF(T^*) = \frac{v_{RATIO}(T)}{k_{ref}}. \qquad (8)$$

Figure 7:
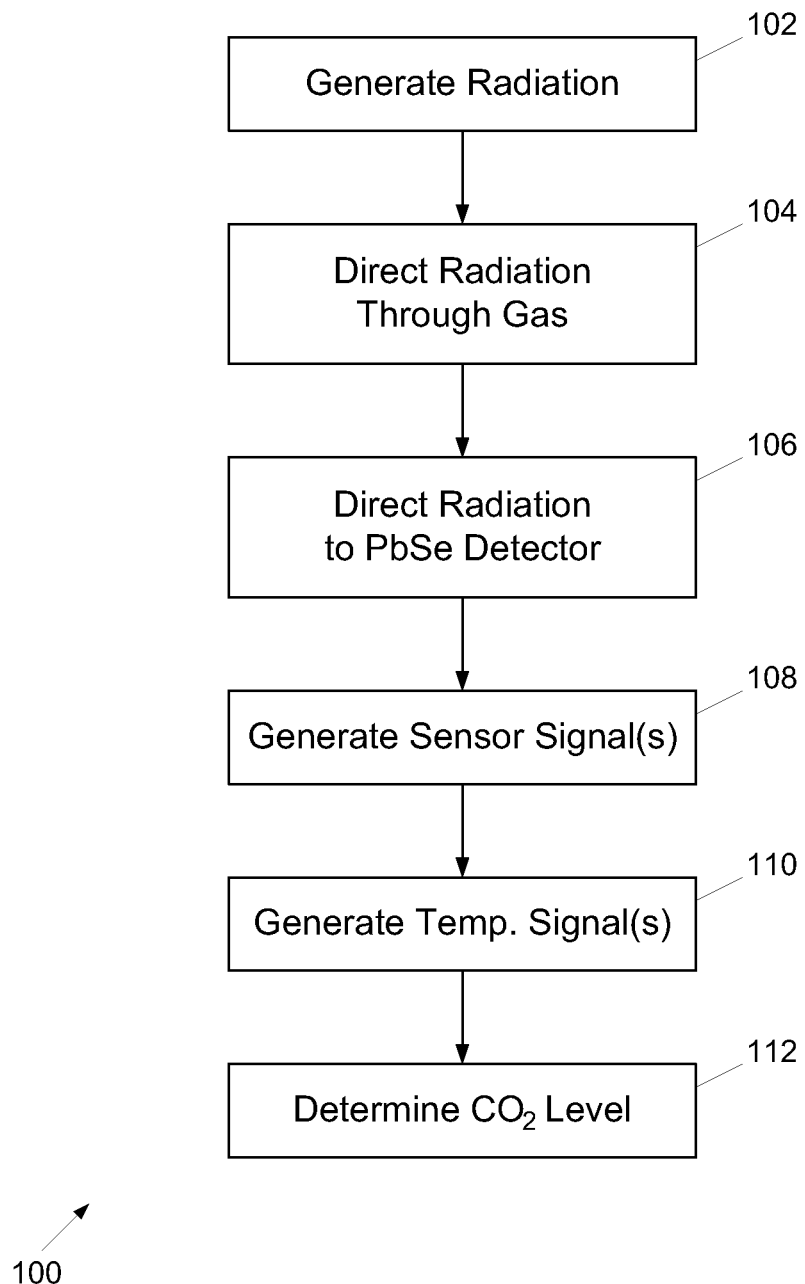
FIG. 7 illustrates a method of detecting a level of carbon dioxide in a body of gas.

FIG. 7 illustrates a method 100 of detecting a level of carbon dioxide in a body of gas. The operations of method 100 presented below are intended to be illustrative. In some embodiments, method 100 may be accomplished with one or more additional operations not described, and/or without one or more of the operations discussed. Additionally, the order in which the operations of method 100 are illustrated in FIG. 7 and described below is not intended to be limiting.

In some embodiments, method 100 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 100 in response to instructions stored electronically on an electronic storage medium. The one or more processing devices may include one or more devices configured through hardware, firmware, and/or software to be specifically designed for execution of one or more of the operations of method 100.

At an operation 102, electromagnetic radiation is generated. The electromagnetic radiation includes radiation at a first wavelength and radiation at a second wavelength. In one embodiment, operation 102 is performed by a radiation source similar to or the same as radiation source 18 (shown in FIG. 1 and described above).

At an operation 104, the electromagnetic radiation is directed through a body of gas. In one embodiment, operation 104 is performed by optics similar to or the same as optics 20 (shown in FIG. 1 and described above).

At an operation 106, the electromagnetic radiation is directed to a lead selenide detector. Directing the electromagnetic radiation to the lead selenide detector may include directing a first portion of the electromagnetic radiation to a first lead selenide detector and directing a second portion of the electromagnetic radiation to a second lead selenide detector. The first portion of electromagnetic radiation may include electromagnetic radiation at the first wavelength. The second portion of electromagnetic radiation may include electromagnetic radiation at the second wavelength. In one embodiment, operation 106 is performed by optics similar to or the same as optics 30 (shown in FIG. 1 and described above).

At an operation 108, one or more sensor signals may be generated. Each sensor signal conveys information related to the intensity of electromagnetic radiation on a corresponding lead selenide detector. This may include generating a first sensor signal corresponding to the first lead selenide detector and a second sensor signal corresponding to the second lead selenide detector. In one embodiment, operation 110 is performed by sensors similar to or the same as the sensors including first lead selenide detector 32 and second lead selenide detector 34 (shown in FIGS. 1 and 2, and described above).

At an operation 110, one or more temperature signals are generated. The temperature signals convey information related to the temperature of one or more of the lead selenide detectors. For example, operation 110 may involve generating a single temperature signal corresponding to both the first lead selenide detector and the second lead selenide detector, operation 110 may involve generating a temperature signal corresponding to each of the first and second lead selenide detectors, and/or operation 110 may involve generating other temperature signals. In one embodiment, operation 110 is performed by thermal sensor 36 (shown in FIGS. 1 and 2, and described above).

At an operation 112, the level of carbon dioxide in the body of gas is determined based on the sensor signal(s) generated at operation 108. The determination of the level of carbon dioxide includes a compensation that adjusts the determination for the temperature of the lead selenide detector(s) (e.g., as conveyed in the temperature signal(s)). In one embodiment, operation 112 is performed by a processor similar to or the same as processor 62 (shown in FIG. 2 and described above).

Figure 8:
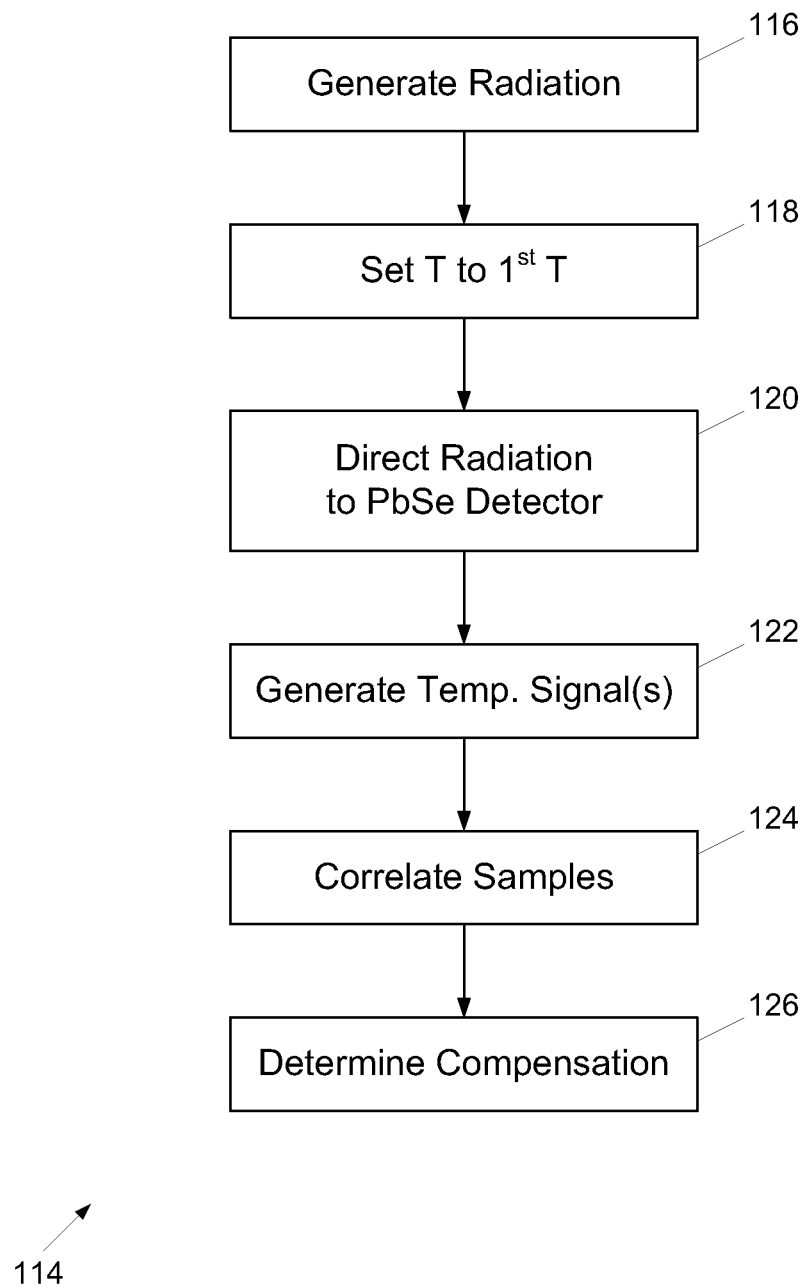
FIG. 8 illustrates a method of calibrating a lead selenide detector.

FIG. 8 illustrates a method 114 of calibrating a lead selenide detector for temperature, wherein the lead selenide detector is configured to generate a detector signal conveying information related to an intensity of electromagnetic radiation incident on a lead selenide sensing element of the lead selenide detector. The operations of method 114 presented below are intended to be illustrative. In some embodiments, method 114 may be accomplished with one or more additional operations not described, and/or without one or more of the operations discussed. Additionally, the order in which the operations of method 114 are illustrated in FIG. 8 and described below is not intended to be limiting.

In some embodiments, method 114 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 114 in response to instructions stored electronically on an electronic storage medium. The one or more processing devices may include one or more devices configured through hardware, firmware, and/or software to be specifically designed for execution of one or more of the operations of method 114.

At an operation 116, electromagnetic radiation is generated. The electromagnetic radiation includes radiation at a first wavelength and radiation at a second wavelength.

At an operation 118, the temperature of the lead selenide detector(s) are controlled over a range of temperatures between a first temperature and a second temperature. In one embodiment, operation 118 is performed by a temperature regulator similar to or the same as temperature regulator 70 (shown in FIG. 3 and described above).

At an operation 120, electromagnetic radiation generated at operation 116 is directed to a lead selenide detector. This may include directing a first portion of the electromagnetic radiation to a first lead selenide detector and directing a second portion of the electromagnetic radiation to a second lead selenide detector. The first portion of electromagnetic radiation may have a first wavelength and the second portion of the electromagnetic radiation may have a second wavelength.

At an operation 122, one or more temperature signals are generated. The temperature signals convey information related to one or more of the lead selenide detectors. In one embodiment operation 122 is performed by a thermal sensor similar to or the same as thermal sensor 68 (shown in FIG. 3 and described above).

At an operation 124, samples of sensor signals generated by via the lead selenide detector(s) are correlated with contemporaneous samples of the temperature signals generated at operation 122. The sensor signals may be similar to or the same as the sensor signals described above with respect to lead selenide detector 67 (shown in FIG. 3 and described above). The correlation of signal samples at operation 124 is performed as the temperature of the lead selenide detector(s) migrates between the first temperature and the second temperature. In one embodiment, the correlation of signal samples at operation 124 is performed by a correlator similar to or the same as correlator 72 (shown in FIG. 3 and described above).

At an operation 126, a compensation that compensates for changes in the sensor signal(s) caused by changes in temperature of the lead selenide detector(s) is determined. In one embodiment, operation 126 is performed by a processor similar to or the same as processor 74 (shown in FIG. 3 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A sensor device configured to measure a level of carbon dioxide in a body of gas, the sensor device comprising:
   a radiation source configured to emit electromagnetic radiation through a body of gas;
   a sensor comprising a first lead selenide detector configured to allow the electromagnetic radiation emitted by the radiation source that has passed through the body of gas to become incident on the first lead selenide detector, the sensor being further configured to generate a first signal conveying information related to an intensity of electromagnetic radiation incident on the first lead selenide detector;

a processor configured to determine the level of carbon dioxide in the body of gas based on the first signal generated by the sensor; and a first thermal sensor that is discrete from the first lead selenide detector and is configured to output a first temperature signal conveying information related to a temperature of the first lead selenide detector, wherein the processor is further configured to determine the level of carbon dioxide further based on a compensation for the temperature of the first lead selenide detector as reflected in the first temperature signal by compensating the first signal directly provided to the processor from the sensor.

2. The sensor device of claim 1, wherein the sensor is further configured to allow the temperature of the first lead selenide detector to drift with a temperature in the sensor device.

3. The sensor device of claim 1, wherein the sensor further comprises a second lead selenide detector configured to receive a portion of the electromagnetic radiation emitted by the radiation source after the electromagnetic radiation has passed through the body of gas, wherein the sensor is further configured to generate a second signal conveying information related to an intensity of electromagnetic radiation incident on the second lead selenide detector, and wherein the processor is further configured to determine the level of carbon dioxide in the body of gas further based on the second signal.

4. The sensor device of claim 3, further comprising a second thermal sensor configured to output a second temperature signal conveying information related to a temperature of the second lead selenide detector, wherein the first and second thermal sensors each separately monitor an individual one of the first and second lead selenide detectors.

5. The sensor device of claim 4, wherein the processor is further configured to determine the level of carbon dioxide further based on a compensation for the temperature of the second lead selenide detector as reflected in the second temperature signal by compensating the second signal directly provided to the processor from the sensor.

6. A method of detecting a level of carbon dioxide in a body of gas, the method comprising acts of:

emitting electromagnetic radiation through a body of gas by a radiation source;

receiving electromagnetic radiation that has passed through the body of gas on a first lead selenide detector of a sensor;

generating a first sensor signal by the sensor conveying information related to an intensity of electromagnetic radiation incident on the first lead selenide detector;

generating a first temperature signal via a first thermal sensor that is discrete from the first lead selenide detector, the first temperature signal conveying information related to a temperature of the first lead selenide detector; and determining by a processor the level of carbon dioxide in the body of gas based on the first sensor signal, wherein the determining act involves a compensation for the temperature of the first lead selenide detector as reflected in the first temperature signal by compensating the first sensor signal directly provided to the processor from the sensor.

7. The method of claim 6, further comprising an act of allowing the temperature of the first lead selenide detector to drift.

8. The method of claim 6, further comprising acts of:

receiving electromagnetic radiation that has passed through the body of gas on a second lead selenide detector of the sensor; and generating a second sensor signal by the sensor conveying information related to an intensity of electromagnetic radiation incident on the second lead selenide detector, wherein the determining act is further based on the second sensor signal.

9. The method of claim 6, further comprising an act of generating a second temperature signal via a second thermal sensor, the second temperature signal conveying information related to a temperature of the second lead selenide detector, wherein the first and second thermal sensors each separately monitor an individual one of the first and second lead selenide detectors.

10. The method of claim 9, wherein the determining act further involves a compensation for the temperature of the second lead selenide detector as reflected in the second temperature signal by compensating the second sensor signal directly provided to the processor from the sensor.

11. A system for detecting a level of carbon dioxide in a body of gas, the system comprising:

means for emitting electromagnetic radiation through a body of gas;

means for directing the electromagnetic radiation that has passed through the body of gas onto a first lead selenide detector of a sensor;

means for generating a first sensor signal conveying information related to an intensity of electromagnetic radiation incident on the first lead selenide detector;

means for generating a first temperature signal that is discrete from the first lead selenide detector, the first temperature signal conveying information related to a temperature of the first lead selenide detector; and means for determining the level of carbon dioxide in the body of gas based on the first sensor signal, wherein the means for determining involves a compensation for the temperature of the first lead selenide detector as reflected in the first temperature signal by compensating the first sensor signal directly provided to the means for determining from the sensor.

12. The system of claim 11, wherein the temperature of the first lead selenide detector is allowed to drift.

13. The system of claim 11, further comprising:

means for directing electromagnetic radiation that has passed through the body of gas on a second lead selenide detector of a sensor; and means for generating a second sensor signal conveying information related to an intensity of electromagnetic radiation incident on the second lead selenide detector, wherein the means for determining is further configured such that the determination of the level of carbon dioxide in the body of gas is further based on the second sensor signal.

14. The system of claim 11, further comprising means for generating a second temperature signal, the second temperature signal conveying information related to a temperature of the second lead selenide detector.

15. The system of claim 14, wherein the means for determining is further configured such that the determination of the level of carbon dioxide further involves a compensation for the temperature of the second lead selenide detector as reflected in the second temperature signal by compensating the second sensor signal directly provided to the means for determining from the sensor.

16. The sensor device of claim 5, wherein the first signal and the second signal are compensated individually.

17. The method of claim 10, wherein the first sensor signal and the second sensor signal are compensated individually.

* * * * *